United States Patent
O'Connor et al.

(10) Patent No.: US 8,613,546 B2
(45) Date of Patent: Dec. 24, 2013

(54) CLEANING APPARATUS AND/OR CLEANING TECHNIQUES FOR USE WITH A RADIATION SYSTEM

(75) Inventors: John P. O'Connor, Andover, MA (US); Charles Shaughnessy, Hamilton, MA (US); Sorin Marcovici, Lexington, MA (US)

(73) Assignee: Analogic Corporation, Peabody, MA (US)

( * ) Notice: Subject to any disclaimer, the term of this patent is extended or adjusted under 35 U.S.C. 154(b) by 374 days.

(21) Appl. No.: 13/017,938

(22) Filed: Jan. 31, 2011

(65) Prior Publication Data

US 2012/0195410 A1     Aug. 2, 2012

(51) Int. Cl.
*H05G 1/02* (2006.01)
*H05G 1/00* (2006.01)

(52) U.S. Cl.
USPC .......................................... 378/204; 378/210

(58) Field of Classification Search
USPC ............ 378/4–20, 91, 95, 193–204, 210, 901
See application file for complete search history.

(56) References Cited

U.S. PATENT DOCUMENTS 7,254,438 B2 *   8/2007   DeSilets et al. ................ 600/427

FOREIGN PATENT DOCUMENTS

JP         7148147         6/1995

* cited by examiner

*Primary Examiner* — Anastasia Midkiff
(74) *Attorney, Agent, or Firm* — Cooper Legal Group LLC (57) ABSTRACT

One or more techniques and/or systems are described herein for cleaning a portion of a radiographic examination apparatus whereon debris may accumulate. Typically, the portion being cleaned is within a scanning field of the radiographic examination device (e.g., within a portion of the radiographic examination device through which radiation traverses). Activation of a cleaning mechanism, or a portion thereof, may be timed to miss radiation emitted during a scan, and thus not interfere with a scan. Also, the cleaning mechanism, or a portion thereof, may be located so as to not attenuate radiation. If radiation is attenuated by the cleaning mechanism corrective techniques can be implemented to account for such attenuation.

22 Claims, 6 Drawing Sheets

CLEANING APPARATUS AND/OR CLEANING TECHNIQUES FOR USE WITH A RADIATION SYSTEM

BACKGROUND

The present application relates to techniques and/or systems for cleaning a portion of a shroud (e.g., within and/or adjacent a scanning view) of a radiographic examination device. It finds particular application with computed tomography (CT) scanners that are used in industrial applications (e.g., such as in the lumber industry), but it also relates to other types of radiographic examination devices (e.g., line scanners, projection scanners, etc.) and/or other applications (e.g., medical, security, etc.) where debris (e.g., particulates, fluid, etc.) may accumulate between an object under examination and a detector array and/or between the object under examination and a radiation source of the radiographic examination device.

Radiographic imaging systems, or more generally, radiographic examination devices, such as projection radiography systems, computed tomography (CT) systems, line scanners, etc., provide information, or images, of the inside of an object under examination (e.g., interior aspects of an object under examination). That is, an object under examination by the radiographic examination device is exposed to radiation, and one or more images are formed based upon the radiation absorbed by the object, or rather an amount of radiation that is able to pass through the object. Typically, highly dense objects absorb (e.g., attenuate) more radiation than less dense objects, and thus an object having a higher density, such as a bone or metal object, for example, will appear differently than less dense objects, such as fatty tissue or clothing, for example.

A detector array, generally positioned opposite a radiation source from which radiation is emitted relative the object under examination, is configured to detect radiation that traverses the object under examination and convert such radiation into signals and/or data that may be processed to produce the image(s). Such an image(s) may be viewed by security personnel to detect threat items (e.g., weapons, etc.), viewed by medical personnel to detect medical conditions (e.g., cancerous tissue), and/or viewed by industrial analyst to identify application specific features. For example, a lumber mill may use a radiographic examination device to identify knots in a tree and/or a butcher may use a radiographic examination device to identify fat in meat. In this way, the cuts to the lumber or to the meat can be improved to reduce the amount of valuable lumber and/or meat that may otherwise be wasted, for example.

While the applications for radiographic examination devices are nearly endless, implementation challenges have arisen that make it difficult to effectively utilize radiographic examination devices in some applications. For example, in dirty and/or dusty environments (such as lumber mills), debris (e.g., wood chips) can accumulate between the object under examination and the detector array and/or between the object under examination and the radiation source. Further, even in more sterile environments, such as meat processing plants, fluids (e.g., blood) and/or particulates may accumulate within a scanning view and/or around an examination region of the radiographic examination device. Such debris, fluids, etc. may interfere with the radiation, causing aspects within the object to be mischaracterized (e.g., as a knot, lean meat, etc.), and/or reducing the quality of resulting images/information acquired from the radiographic examination.

SUMMARY

Aspects of the present application address the above matters, and others. According to one aspect an apparatus for cleaning a radiographic examination device is provided. The apparatus comprises a cleaning mechanism configured to clean at least a portion of a shroud of the radiographic examination device. The portion of the shroud to be cleaned is situated at least one of between an object under examination and a detector array of the radiographic examination device and between the object under examination and a radiation source of the radiographic examination device.

According to another aspect, a method for cleaning a radiographic examination device is provided. The method comprises beginning an examination of an object under examination using the radiographic examination device. The method also comprises cleaning a portion of the radiographic examination device through which radiation traverses during the examination. The method further comprises ending the examination of the object.

According to yet another aspect, a method for cleaning a radiographic examination device is provided. The method comprises activating a cleaning mechanism to clean a portion of the radiographic examination device through which radiation traverses and whereon debris accumulates. The method also comprises cleaning the portion of the radiographic examination device.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for cleaning a portion of a shroud of a radiographic examination device are provided. Generally, the shroud is within and/or surrounds a scanning field in which radiation impinges, and, in one embodiment, may be cleaned during a radiographic examination (e.g., while radiation is being emitted). As described herein, numerous techniques and/or mechanisms are contemplated for cleaning the shroud that may be used alone and/or in combination with one or more other mechanisms and/or techniques. For example, in one embodiment, a wiper blade or brush is configured to periodically clean the shroud. In another embodiment, one or more gases and/or one or more fluids, such as air and/or water may be dispensed to periodically clean the shroud. In yet another embodiment, a device may be configured to suction particulates and/or fluid off the shroud. Other such techniques and/or mechanisms may be evident from the description herein.

Figure 1:
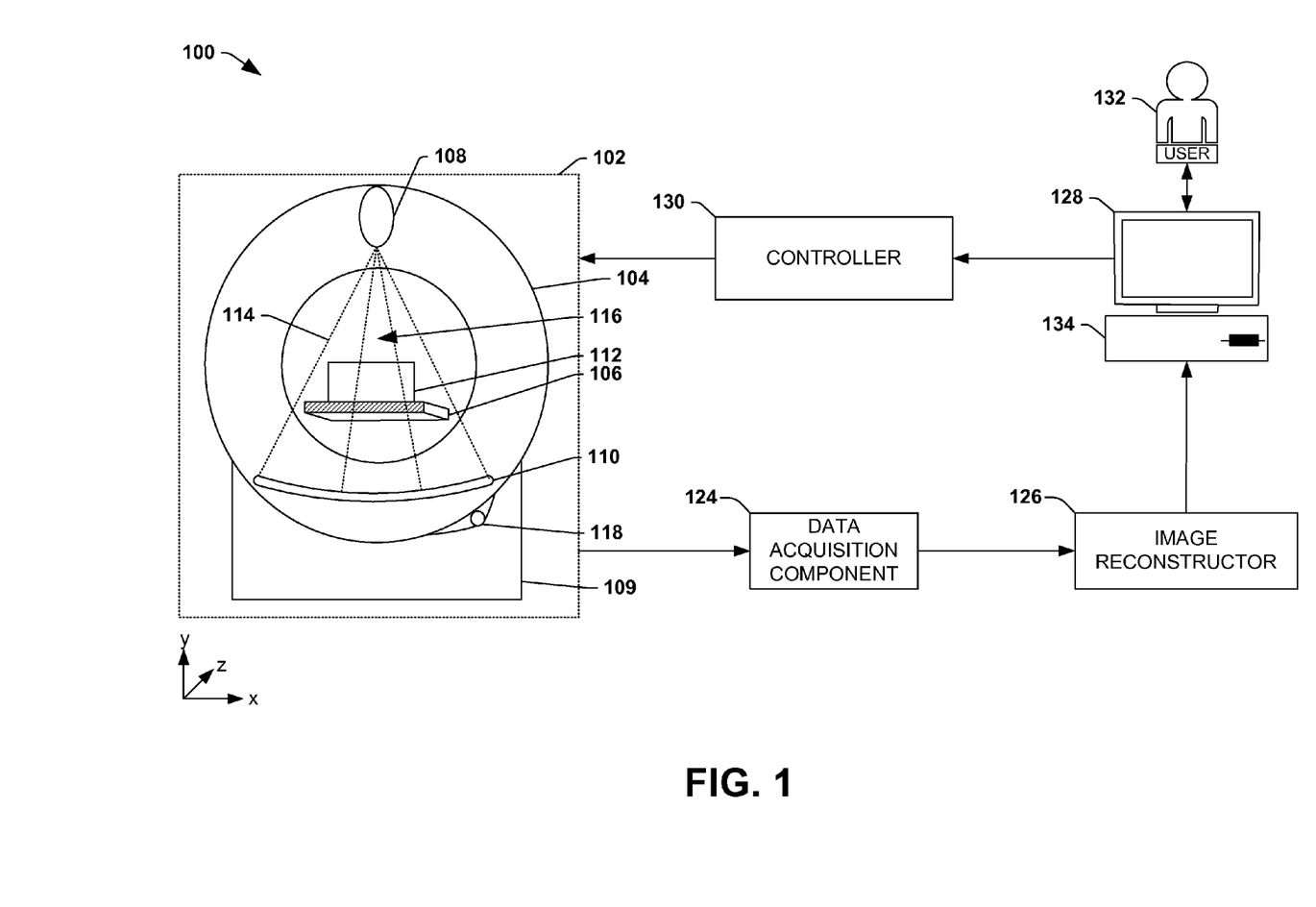
FIG. 1 is a schematic block diagram illustrating a radiographic examination apparatus.

FIG. 1 is an illustration of an example environment 100 in which data that is generated from components comprised within a rotating gantry 104 of a radiographic examination device (e.g., a CT scanner) may be acquired so that one or more images of an object 112 under examination may be produced and displayed on a monitor 128, for example, such as for viewing by a human user 132. Such a device may be used to identify a tumor in a human patient at a medical center or in an animal at a veterinary clinic, and/or to identify objects of interest (e.g., potential threat objects, banned objects) associated with (e.g., comprising, comprised within, etc.) an object 112 (e.g., luggage) under examination at a security checkpoint, for example. In another embodiment, no image is generated, but the density and/or atomic characteristics of the object 112 can be identified and compared with a list of densities and/or atomic characteristics associated with predetermined items (e.g., banned items) to determine if the object 112 potentially comprises one or more of the predetermined items. Similarly, in other applications, the density and/or atomic characteristics can be identified and used to improve (e.g., optimize) operations to the object 112 under examination. For example, in a lumber or meat processing application, the density and/or atomic characteristics can be used to identify undesirable portions of the object and to plan cuts accordingly (e.g., to minimize the amount of desirable portions of the lumber and/or meat that is wasted).

It will be appreciated that while a CT scanner is described herein, the instant application is not intended to be so limited. That is, to the extent possible, the instant application, including the scope of the claimed subject matter, is intended to be applicable to other systems as well. For example, the claimed subject matter is intended to be applicable to other radiographic systems, such as, projection radiography, line scanners, etc. It will also be appreciated that the example environment 100 merely illustrates an example schematic and is not intended to be interpreted as necessarily specifying the orientation/position of the components described herein. For example, a data acquisition component 124 as illustrated in FIG. 1, may be part of the rotating gantry 104 portion of the radiographic examination device, or more particularly, may be part of a detector array 110 of the radiographic examination device.

In the example environment 100, the radiographic examination device comprises an object examination apparatus 102 configured to examine one or more objects 112 (e.g., a series of suitcases at an airport, a human patient, a series of pieces of lumber, a series of pieces of meat, etc.). The object examination apparatus 102 can comprise a rotating gantry 104 and a stationary portion 109. During an examination of the object(s) 112, the object(s) 112 can be placed on a support article 106, such as a bed or conveyor belt, that is selectively positioned in an examination region 116 (e.g., a hollow bore in the rotating gantry portion 104), and the rotating gantry 104 can be rotated about the object(s) 112 by a rotator 118 (e.g., motor, drive shaft, chain, etc.).

The rotating gantry 104 may surround a portion of the examination region 116 and comprises a radiation source 108 (e.g., an ionizing x-ray source) and a detector array 110 that is mounted on a substantially diametrically opposite side of the rotating gantry 104 relative to the radiation source 108.

During an examination of the object(s) 112, the radiation source 108 emits radiation 114 towards the object(s) 112 under examination while the rotating gantry 104 (including the radiation source 108 and/or the detector array 110) rotates about the object(s) 112. Generally, in a CT scanner, the radiation 114 is emitted substantially continuously during the examination. However, in some CT scanners and/or in other radiography imaging devices (e.g., pulsed radiographic scanners), the radiation 114 may be emitted intermittently during the rotation.

As the radiation 114 traverses the object(s) 112, the radiation 114 may be attenuated differently by different aspects of the object(s) 112. Because different aspects attenuate different percentages of the radiation 114, an image may be reconstructed based upon the attenuation, or rather the variations in the number of photons that are detected by the detector array 110. For example, more dense aspects of the object(s) 112, such as a bone, metal plate, or a knot in a piece of wood, for example, may attenuate more of the radiation 114 (e.g., causing fewer photons to strike the detector array 110) than less dense aspects, such as skin, clothing, or healthy portions of the wood.

In some embodiments, while the object(s) 112 is being examined, the object(s) 112 may be translated along an axis traveling in the z-dimension (e.g., into and out of the page if, as illustrated, the rotating gantry 104 is configured to rotate in an x, y plane). In this way, an object 112 that has a z-dimension greater than the z-dimension of the radiation traversing the object may be examined more quickly (relative to a step-and-shoot scanning approach). It will be appreciated that if the object(s) 112 is being translated (e.g., in the z direction) during an examination while the rotating gantry 104 is rotating (e.g., in the x, y plane), the examination may be referred to as a helical or spiral scan.

The detector array 110 is configured to convert the radiation photons into electric charge that may be detected by one or more pixels, or elements, of the detector array 110 that are in close spatial proximity to the location where the radiation impinged. It will be appreciated to those skilled in the art that the detector array 110 may be a direct conversion detector array (e.g., a detector array comprised of amorphous selenium, crystalline materials, etc.) configured to convert radiation directly into electric charge or an indirect conversion detector array (e.g., a detector array comprised of a scintillator and a photodetector array) configured to convert radiation into an intermediary medium (such as light) before being converted into electric charge.

The detector array 110, regardless of whether it is a direct conversion or indirect conversion array, is generally comprised of a pixelated array (e.g., a thin-film transistor array, complementary metal-oxide-semiconductor array, etc.) configured to detect and/or measure electric charge yielded from the detected radiation. Respective pixels, or channels, generate a signal (e.g., generally in an analog domain) indicative of the electric charge detected, which is fed to a data acquisition component 124. Because the electric charge detected by the one or more pixels is directly related to the number of photons (e.g., an electric charge of about 1200 electrons may be equivalent to one radiation photon), the output is indicative of the attenuation of the radiation 114 as it traversed the object(s) 112. It will be appreciated that, in one embodiment, when a pixel is not detecting electric charge, the pixel can emit a baseline signal that indicates that the pixel has detected little to no electric charge. In another embodiment, respective pixels do not emit a signal unless and/or until electric charge is detected by the pixel.

Signals that are produced by pixels of the detector array 110 can be transmitted from the detector array 110 to a data acquisition component 124 configured to compile signals that were transmitted within a predetermined time interval, or measurement interval, using techniques known to those skilled in the art (e.g., binning, integration, etc.). It will be appreciated that such a measurement interval may be referred to as a "view" and generally reflects signals generated from radiation 114 that was emitted while the radiation source 108 was at a particular angular range relative to the object 112. Based upon the compiled signals, the data acquisition component 124 can generate projection data indicative of the compiled signals, for example.

Moreover, it will be understood to those skilled in the art that in some embodiments, such as where the pixels of the detector array 110 emit an analog signal, the radiographic examination device may comprise an analog to digital (A/D) signal converter (not shown, but generally operably coupled with or comprised within the detector array 110 and/or the data acquisition component 124) configured to receive the analog signals and convert the signals into digital signals. The data comprised in the digital signals may be formatted in any one or more of a number of different formats, such as a 16-bit floating-point format, a quasi-logarithmic format, and/or a non-linear digital format, etc. Data comprised in the digital signals is commonly referred to in the art as projection space data because, like the analog signals, the digital signals are in projection space, and may represent an indication of how many photons are detected by a pixel.

The example environment 100 further comprises an image reconstructor 126 configured to receive the projection data that is output by the data acquisition component 124. The image reconstructor 126 is configured to generate image data from the projection data using a suitable analytical, iterative, and/or other reconstruction technique known to those skilled in the art (e.g., 2D filtered backprojection, tomosynthesis reconstruction, etc.). In this way, the data is converted from projection space to image space, a domain that may be more understandable by a user 132 viewing the image(s), for example.

The example environment 100 also comprises a workstation 134 (e.g., a computer) configured to receive the image(s), which can be displayed on the monitor 128 to the user 132 (e.g., security personnel, medical personnel, industrial analyst etc.). In this way, a user 132 can inspect the image(s) to identify areas of interest within the object(s) 112. The workstation 134 can also be configured to receive user input which can direct operations of the object examination apparatus 102 (e.g., a speed to rotate, a speed of a conveyor belt, etc.).

It will be appreciated that in another embodiment, no images are generated (e.g., the radiographic examination device does not comprise an image reconstructor 126) and the workstation 134 is merely configured to identify areas of the object under examination 112 that are undesirable and/or desirable for a given application. For example, a workstation 134 of a radiographic examination device in a lumber mill may be configured to identify portions of the examined lumber (e.g., the object under examination) that comprise knots or other irregularities (such as nails). Moreover, in one embodiment, the workstation 134 can be configured to perform other measurements and/or calculations. For example, returning to the lumber mill application, the workstation 134 may be configured to strategically plan a cut pattern for the piece of lumber under examination such that the amount of desirable lumber that is wasted is mitigated.

In the example environment 100, a controller 130 is operably coupled to the workstation 134. In one example, the controller 130 is configured to receive user input from the workstation 134 and generate instructions for the object examination apparatus 102 indicative of operations to be performed. For example, the user 132 may want to reexamine the object(s) 112, and the controller 130 may issue a command instructing the support article 106 to reverse direction (e.g., bringing the object(s) 112 back into an examination region 116 of the object examination apparatus 102).

Figure 2:
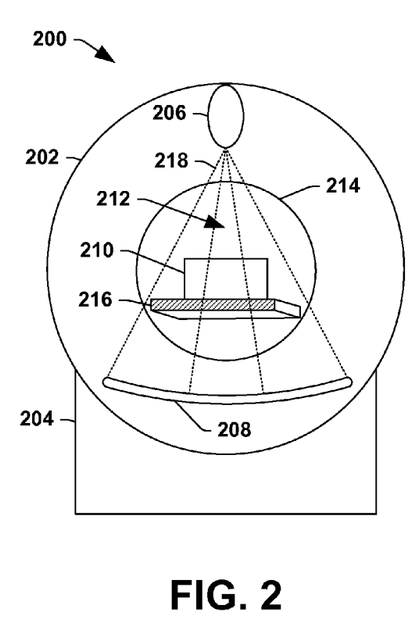
FIG. 2 illustrates a two-dimensional view of an example object examination apparatus.
Figure 3:
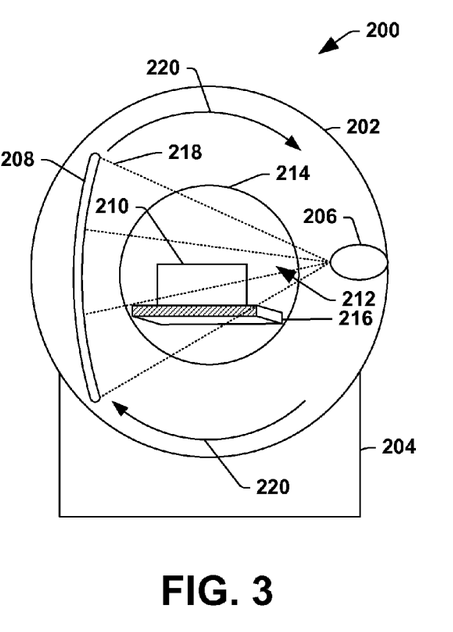
FIG. 3 illustrates a two-dimensional view of an example object examination apparatus.

FIGS. 2-3 illustrate an example rotation of an object examination apparatus 200 (e.g., 102 in FIG. 1), such as may occur during a computed tomography (CT) examination, for example. As illustrated, the object examination apparatus 200 comprises a rotating gantry (e.g., 104 in FIG. 1) and a stationary portion 204 (e.g., 109 in FIG. 1). Generally, the rotating gantry, which is physically coupled to a radiation source 206 (e.g., 108 in FIG. 1) and/or a detector array 208 (e.g., 110 in FIG. 1) is surrounded by a substantially stationary shroud 202 (e.g., a non-rotating shroud) comprised of a material that is substantially transparent to radiation, and as described herein, may be comprised of an antistatic material (e.g., an antistatic plastic). Thus, the rotating gantry (and the radiation source 206 and the detector array 208) is generally hidden from view once the object examination apparatus 200 is manufactured and the shroud 202 is put in place. It will be appreciated that for the purposes of clarity, the rotating gantry is not illustrated, but is generally comprised of a structure configured to connect the radiation source 206 to the detector array 208 and, in one embodiment, may cause the radiation source 206 and the detector array 208 to rotate synchronously, for example. In this way, in this embodiment, the radiation source 206 may remain at a substantially fixed orientation relative to the detector array 208 while rotating relative to an object(s) 210 (e.g., 112 in FIG. 1) under examination and/or relative to a substantially stationary shroud 202 surrounding and/or encasing the rotating gantry, for example.

Generally, the object(s) 210 under examination is inserted into and/or supported in an examination region 212 (e.g., generally defined by an inner surface 214 in the substantially stationary shroud 202 (e.g., such that a bore is formed through the center of the substantially stationary shroud)) by a support article 216, such as a conveyor belt and/or medical bed, for example, and radiation 218 is emitted from the radiation source 206. Radiation that traverses the object(s) 210 under examination is generally detected by the detector array 208 positioned on an opposite side of the object(s) 210 under examination relative to the radiation source 206.

As radiation 218 is being emitted, the rotating gantry rotates causing the radiation source 206 and detector array 208 to be rotated 220 relative to the object(s) 210 under examination as illustrated in FIG. 3. Generally, as described above, the radiation source 206 and the detector array 208 rotate such that their relative position to one another remains substantially fixed. In this way, the object(s) 210 under examination may be viewed from a plurality of angles, for example, such that volumetric data representative of the object 210 under examination may be generated and/or images representative of a portion of the object 210 under examination (e.g., representative of a slice of the object) may be generated (e.g., using tomosynthesis reconstruction). It will be appreciated that while FIG. 3 illustrates the radiation source 206 and detector array 208 being rotated 220 clockwise relative to the object(s) 210 under examination, in another embodiment, the radiation source 206 and/or the detector array 208 may be rotated counter-clockwise relative to the object(s) 210 under examination.

In yet another embodiment, the object(s) 210 under examination may be viewed from a plurality of angles without rotating both the radiation source 206 and the detector array 208. For example, in some embodiments, volumetric data representative of object(s) 210 under examination may be generated by rotating the radiation source 206 or the detector array 208, but not both. For example, the radiation source 206 may rotate 20 to 30 degrees left and right of center while the detector array 208 is held at a substantially fixed position/orientation relative to the object(s) 210 under examination. Thus, in some embodiments, the orientation of the radiation source 206 relative to the detector array 208 may not be fixed.

In yet another embodiment (e.g., a line scanner), neither the radiation source 206 nor the detector array 208 may move relative to the object(s) 210 under examination, and two-dimensional projection data of the object(s) 210 under examination may be yielded from the examination (e.g., as opposed to three-dimensional, volumetric data). It will be appreciated that to generate volumetric data of the object(s) 210 under examination when neither the radiation source 206 nor the detector array 208 rotate, the object(s) 210 may be rotated (e.g., within the examination region 212). Thus, the orientation of the radiation source 206 and/or detector array 208 changes relative to the object(s) 210 under examination without rotating either the radiation source 206 or the detector array 208. Moreover, it will be appreciated that one or more of the aforementioned techniques may be combined in the example object examination apparatus. For example, the object(s) 212 may be rotated in the examination region 212 and the radiation source 206 may rotate while the detector array 208 remains in a relatively fixed position.

Figure 4:
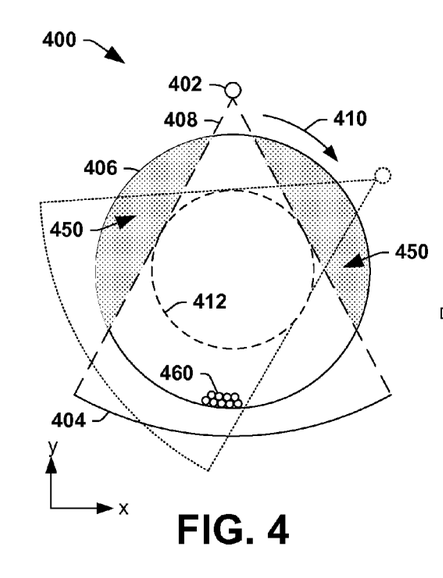
FIG. 4 illustrates a beamline geometry of an example radiographic examination apparatus.

FIG. 4 illustrates a beamline geometry 400 of an examination object examination apparatus (e.g., 200 in FIGS. 2-3), such as a CT scanner, for example. More specifically, FIG. 4 illustrates an example radiation source 402 (e.g. 206 in FIGS. 2-3) and detector array 404 (e.g., 208 in FIGS. 2-3) configured to rotate about an object that is situated within a bore (defined by an inner wall 406 (e.g., 214 in FIG. 2) of a substantially stationary shroud that surrounds a rotating gantry portion of a radiographic examination device). It will be appreciated that the different illustrations provided herein may not be to scale relative to one another (or otherwise). For example, the bore (defined by shroud inner sidewall 406) in FIG. 4 may be larger than the bore (defined by shroud inner sidewall 214) in FIG. 2.

As illustrated, radiation 408 is generally emitted as a fan or cone-shaped beam (e.g., where a cone beam is defined as having a substantially larger z-dimension than a fan beam, which may have virtually no z-dimension). The x-dimension of the fan and/or cone beam is generally substantially equal to the x-dimension of the detector array 404, such that substantially the entire surface of the detector array 404 may receive radiation 408 emitted from the radiation source 402.

As the radiation source 402 and/or the detector array 404 rotate 410 about an object under examination (e.g., situated in the bore) as illustrated in FIGS. 2 and 3, an "interior" portion 412 of the bore, referred to as a field of view, remains substantially constantly exposed to radiation during the entire examination. Conversely, an "exterior" portion of the bore, having a diameter larger than the diameter of the "interior" portion of the bore, periodically receives virtually no radiation. For example, when the radiation source 402 is in an upright position, as is illustrated in FIG. 4, the (shaded) portions 450 of the bore lie outside the "wedge" of radiation 408 and thus receive little to no radiation.

It will be appreciated that as used herein, the terms "scanning field" and the like refer to any portion of the bore that receives radiation both substantially continually, such as "interior" portion 412, and/or intermittently, such as "exterior" portion(s) 450, whereas the terms "field of view" and the like merely refer to "interior" portion 412 of the bore that is substantially constantly exposed to radiation.

It will be appreciated that as one or more objects are examined in the bore, particulates 460 and/or fluid may fall off the object and/or otherwise be introduced into the examination region and/or bore and collect on the inner surface or inner sidewall 406 of the substantially stationary shroud. For example, as illustrated, particulates 460 may collect at the bottom of the inner surface 406 due to gravity. Generally, these particulates 460 are within the scanning field of the bore, but outside of a field of view. Thus, these particulates 460 are periodically not exposed to radiation. For example, when the radiation source 402 is emitting radiation substantially horizontally, the particulates 460 would be within a portion of the scanning field receiving little to no radiation (e.g., as described in further detail with respect to FIGS. 8-11).

It will be appreciated that as these particulates 460 (e.g., debris) accumulate, they may interfere with (e.g., attenuate) radiation (e.g., causing less and less radiation to be detected). Stated different, as the amount of particulates 460 increases, image degradation may increase and/or the probability of a misidentification/mischaracterization of an object under examination may increase (e.g., because radiation is being attenuated by particulates 460 that are not part of the object under examination). Thus, as described herein, one or more cleaning mechanisms may be used to clean the scanning field or at least a portion thereof (e.g., to mitigate particulate, fluid, etc. build-up). Moreover, as will be describe in more detail below (e.g., particularly with respect to FIGS. 8-11), one or more of the cleaning techniques and/or devices may utilize the portions of the scanning field that are not exposed to radiation to clean the particulates, fluid, etc. off the scanning field. For example, in one embodiment, a location of the shroud wherein the particulates 460 reside is cleaned at times when this portion of the shroud is within a portion of the scanning field receiving little to no radiation.

Figure 5:
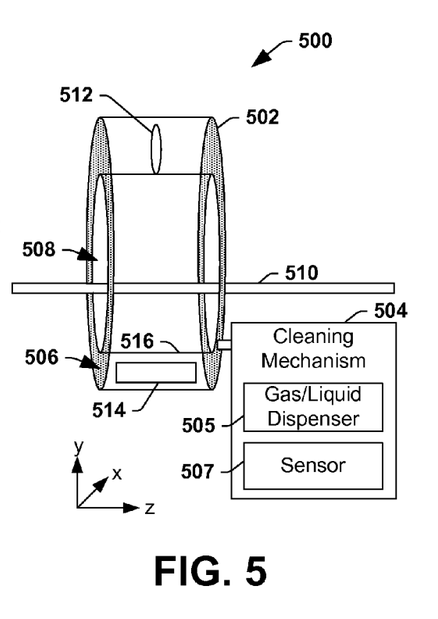
FIG. 5 illustrates a three-dimensional side view of an object examination apparatus and an adjacent cleaning mechanism.

FIG. 5 illustrates an example environment 500 for cleaning a radiographic examination device. Specifically, FIG. 5 illustrates a side-view of an example object examination apparatus 502 (e.g., 102 in FIG. 1) and an adjacent cleaning mechanism 504 configure to clean at least a portion of a shroud 506 of the radiographic examination device.

Stated differently, as illustrated, the shroud 506 surrounds an object examination region (e.g., defined by a bore 508 in the center region of the shroud 506). Generally, an object (not shown) is placed into and/or supported in the examination region (e.g., in the z direction) by a support article 510 (e.g., 106 in FIG. 1), and, during an examination of the object, a radiation source 512 (e.g., 402 in FIG. 4) and/or a detector array 514 (e.g., 404 in FIG. 4) may rotate about the object (e.g., in an x, y plane into and out of the page). In this way, volumetric data of the object under examination may be generated, for example.

As described with respect to FIG. 4, as one or more objects are examined by the object examination apparatus, particulates, fluid, etc. may accumulate on a portion of the shroud between the object under examination and the detector array 514 and/or between the object under examination and the radiation source 512 (e.g., when the radiation source 512 and detector array 514 are "flipped" relative to the orientation illustrated in FIG. 5 such that the radiation source 512 is below the object under examination and support article 510 and the detector array 514 is above the object under examination and support article 510). For example, as illustrated in FIG. 4, due to gravity, the particulates, fluid, etc. (not shown) may accumulate on a bottom surface 516 of the bore (e.g., along an inner edge of the substantially stationary shroud 506 that surrounds the rotating gantry portion of the object examination apparatus 502). Thus, the cleaning mechanism 504 is situated/configured/positioned to clean a portion of the shroud that is positioned between the object examination and the detector array 514 and/or between the object under examination and the radiation source 512 whereon the particulates, fluid, etc. accumulate. For example, as illustrated, the cleaning mechanism 504 is positioned to clean a bottom portion 516 of the bore.

The cleaning mechanism 504 may comprise any number of suitable mechanisms for cleaning a portion of the shroud, and the particular one or more mechanisms used may depend upon the application of the radiographic examination device. For example, in one embodiment, the cleaning mechanism 504 comprises an actuator (e.g., such as a pneumatic actuator and/or an electric actuator) configured to release a gas and/or a fluid and a dispenser 505 (e.g., such as a high pressure nozzle) configured to dispense the released gas and/or fluid towards the portion of the shroud that the cleaning mechanism 504 is positioned to clean (e.g., towards the bottom portion 516 of the bore in the illustrated example). In this way, fluid and/or gas may be used to push the debris and/or fluid across the shroud 506 and out of an opening on the opposite side of the shroud 506 relative to the cleaning mechanism 504. Additionally, the cleaning mechanism 504 may comprise one or more sensors 507 to detect the presence of debris and thus an opportunity to clean. For example, a (laser) beam of light (e.g., from a light source to a light detector) may be present near the bottom surface 516 of the bore such that a break, interruption, etc. in the beam may indicate the presence of debris and thus an opportunity to clean. In yet another embodiment, the actuator of the cleaning mechanism receives information or a signal (e.g., from a workstation 134 in FIG. 1) indicating when to clean. For example, in one embodiment, information yielded from signals generated from pixels near one or more edges of the detector array may be used by the workstation, for example, to detect debris and issue a signal to the cleaning mechanism 504 to begin cleaning the shroud 506. That is, outer edges of the detector array are generally associated with, or rather detect radiation traversing outer portions of the examination region or bore where an object under examination is not located. Accordingly, a change in the amount of radiation detected by such outer edges may be attributable to a build-up of debris and thus serve as a trigger (e.g., or otherwise provide notice) to the cleaning mechanism 504 to begin cleaning In this manner, resources can be conserved by not activating the cleaning mechanism if an opportunity to clean and/or a predetermined amount of debris is not detected.

The cleaning mechanism 504 may, for example, use any gas and/or fluid having properties suitable for cleaning the portion of the shroud 506 that is to be cleaned. For example, in one embodiment, pressurized air is used by the cleaning mechanism 504 to clean the shroud 506. In yet another embodiment, another suitable gas such as helium and/or nitrogen, for example, may be used by the cleaning mechanism 504 to clean the shroud 506. It will be appreciated that where the cleaning mechanism 504 uses a liquid, additional considerations (e.g., besides its effectiveness as a cleaner) may be considered. For example, the cleaning mechanism 504 may use purified water to mitigate the possibility of bacteria being introduced onto the shroud through the liquid (e.g., to mitigate the further build-up of particulates on the portion 516 of the shroud to be cleaned). In another embodiment, drying time of the dispensed liquid is an important consideration to avoid build-up of the cleaning liquid on the portion 516 of the shroud to be cleaned. Thus, a fluid with a faster drying time (e.g., relative to water), such as alcohol, for example, may be used.

Moreover, it will be appreciated that where a fluid is involved, a drain and/or filter may be positioned on the opposite side of the shroud 506 relative to the cleaning mechanism 504 to collect the fluid and return the fluid to the cleaning mechanism (e.g., creating a substantially closed system for the fluid). In this way, the fluid may be recycled to conserve resources, for example. It will also be appreciated that where the cleaning mechanism 504 is configured to dispense fluid, the cleaning mechanism 504 may further comprise a drying component (e.g., such as a gas dispenser) configured to dry the surface of the shroud 506 (e.g., to mitigate fluid building up on the shroud 506). Thus, the cleaning mechanism 504 may comprise a gas dispenser, a liquid dispenser, and/or a gas and liquid dispenser.

In yet another embodiment, the cleaning mechanism 504 may comprise (e.g., in addition to a gas and/or fluid dispenser and/or as a substitute for one or both of these components) a suction mechanism configured to use suction/vacuum properties to pull the debris towards (or away from) the cleaning mechanism 504 (e.g., and into the cleaning mechanism 504 and/or a filter, drain, etc.) from the portion 516 of the shroud 506 that is to be cleaned and an actuator configured to turn on the suction mechanism, for example. In this way, the cleaning mechanism 504 may act substantially similarly to a vacuum, collecting dirt and/or debris from a surface of the shroud 506.

Because the cleaning mechanism 504 is substantially outside of and/or adjacent to the scanning field, the cleaning mechanism 504 may operate to clean the portion 516 of the shroud 506 before, during, and/or after an examination of an object. In one embodiment, if the shroud 506 is cleaned during an examination of the object, for example, the cleaning mechanism 504 may be in operable communication with the object examination apparatus 502 such that the cleaning mechanism 504 can be triggered to power on and/or to clean the portion 516 of the shroud 506 during times when the portion 516 of the shroud 506 is exposed to little to no radiation (e.g., outside the "wedge" of radiation illustrated in FIG. 4). For example, the object examination apparatus 502 (and/or a workstation 134 in FIG. 1) may emit a signal to the cleaning mechanism 504 indicative of the rotational speed, direction, location, etc. of the radiation source 512 and/or the detector array 514, and based upon this information, the cleaning mechanism 504 may be configured to determine intervals of time during which the portion 516 of the shroud to be cleaned is exposed to little to no radiation (e.g. is within regions 450 in FIG. 4). During these intervals (e.g., when the portion 516 to be cleaned is outside the "wedge"), the cleaning mechanism may disperse gas and/or liquid towards the portion 516 that is to be cleaned and/or suction debris from the portion 516 to be cleaned. During intervals when the portion 516 of the shroud 506 to be cleaned is exposed to radiation, the cleaning mechanism may be configured to stop cleaning said portion 516 (e.g., to mitigate interference with an examination).

Figure 6:
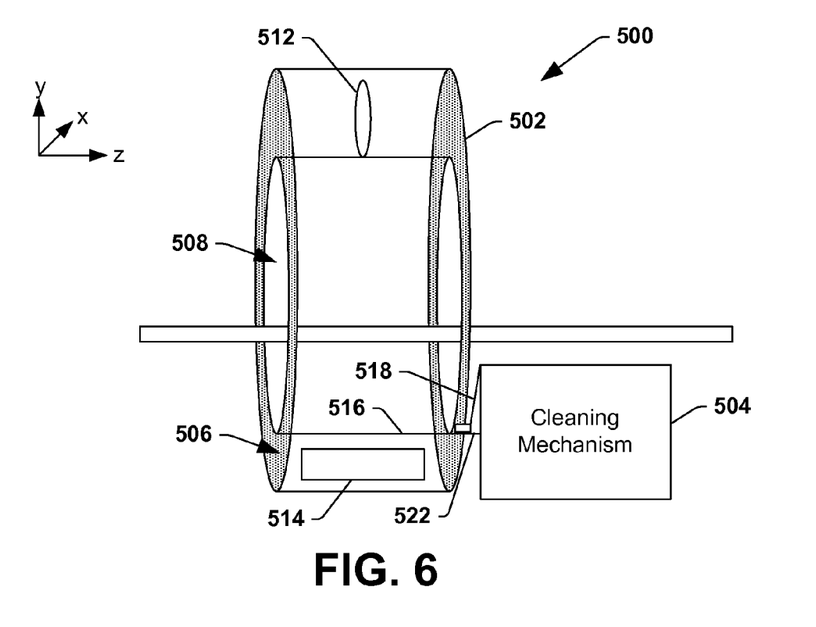
FIG. 6 illustrates a three-dimensional side view of an object examination apparatus and an adjacent cleaning mechanism.
Figure 7:
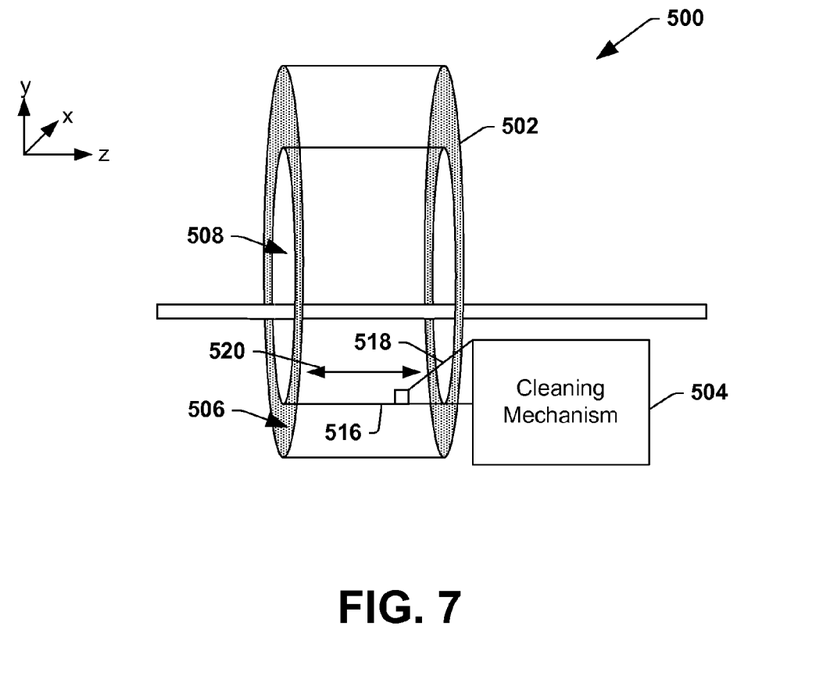
FIG. 7 illustrates a three-dimensional side view of an object examination apparatus and an adjacent cleaning mechanism.

FIGS. 6-7 illustrate yet another embodiment of a cleaning mechanism 504. In this embodiment, the cleaning mechanism 504 comprises a mechanical arm 518, such as a wiper blade or brush configured to wipe and/or brush a portion 516 of the stationary shroud that is, at least sometimes, positioned between an object under examination and a detector array 514 and/or positioned between an object under examination and a radiation source 512. The cleaning mechanism 504 may further comprise an actuator (not shown) configured to control the mechanical arm 518, for example.

As illustrated in FIG. 7, the mechanical arm 518 is configured to extend 520 into (and back out of) the bore 508 (e.g., into the scanning field) to clean the portion 516 of the shroud 506. While such an action is not a problem if the cleaning is performed before and/or after an examination is performed, it will be appreciated that in some embodiments the shroud 506 may need to be cleaned during an examination. In such an embodiment, the mechanical arm 518 may be comprised of a material that is substantially transparent to radiation (e.g., such as a low density plastic). In this way, radiation may pass through the mechanical arm substantially unimpeded, for example. Moreover, it will be appreciated that in an embodiment where the mechanical arm 518 is likely to come into contact with the radiation (e.g., and may attenuate some of the radiation), interpolation, using techniques known to those skilled in the art, can be performed to correct for the attenuation caused by the mechanical arm 518 if the orientation (e.g., position) of the mechanical arm 518 is known. For example, in one embodiment, the cleaning mechanism 504 may relay information about the orientation of the mechanical arm 518 at a given time to a workstation (e.g., 134 in FIG. 1), which is configured to correct images resulting from radiation that was at least partially attenuated by the mechanical arm 518 based upon interpolation techniques known to those skilled in the art.

Thus, where the mechanical arm 518 may attenuate the radiation (e.g., where the mechanical arm 518 is in a portion of the scanning field receiving radiation), numerous techniques known to those skilled in the art may be used to mitigate the attenuation and/or to correct for the attenuation (e.g., after the fact). For example, the mechanical arm 518 may be comprised of a material that is transparent or nearly transparent to radiation such that the amount of radiation attenuated by the mechanical arm 518 is negligible, and/or interpolation may be performed to correct the data and/or resulting image(s) yielded from radiation that was at least partially attenuated by the mechanical arm 518.

In yet another embodiment, the cleaning mechanism 504 and/or the mechanical arm 518 may be synchronized with the rotation of a rotating gantry (e.g., including the radiation source 512 and/or the detector array 514), and may be inserted/extended into the scanning field of the object examination apparatus at times when little to no radiation traverses the portion 516 of the shroud 506 that is to be cleaned. That is, the cleaning mechanism 504 may be in operable communication with the object examination apparatus 500 and/or other components of a radiographic examination device (e.g., such as a workstation 134 in FIG. 1), for example, to identify suitable times when the mechanical arm 518 may enter the scanning field without impeding the examination. For example, as illustrated in FIG. 6, when radiation is traversing the portion 516 of the shroud 506 to be cleaned (e.g., as may be the situation when the detector array 514 is directly below the portion 516 to be cleaned), the mechanical arm 518 may be retracted such that it is outside of the scanning field (e.g., and may reside on a platform 522 adjacent the scanning field (e.g., adjacent the bore 508 in the object examination apparatus 502)). Once the rotating gantry has rotated such that the portion 516 to be cleaned resides in a portion of the scanning field that receives little to no radiation (e.g., 450 in FIG. 4), the mechanical arm 518 may be extended into the scanning field, as illustrated in FIG. 7 (e.g., to "broom away" debris).

Thus, where the mechanical arm 518 is selectively inserted into the scanning field in a manner that causes the mechanical arm 518 to not attenuate radiation, the interpolation techniques described above may not be performed (or may be performed to a lesser degree). Moreover, because the mechanical arm 518 does not come into contact with radiation (e.g., or at least primary radiation that is used to reconstruct an image of the object), the mechanical arm may be constructed of materials that are not transparent to radiation and/or that may cause significant attenuation of radiation (e.g., such as a metal).

It will be appreciated that while the afore-described cleaning mechanisms 504 generally resides adjacent that object examination apparatus and may be stationary, in another embodiment, the cleaning mechanism 504 may be configured to rotate about the object under examination. For example, in one embodiment, the rotating gantry, or a portion thereof, (which may be a metal structure) is extended outside the substantially stationary shroud in which it is generally encased, and the cleaning mechanism 504 is coupled to the rotating gantry. Thus, the cleaning mechanism 504 may rotate synchronously with the rotating gantry, the radiation source 512, and/or the detector array 514. Moreover, a nozzle (e.g., gas or liquid dispense) of the cleaning mechanism 504 and/or a brush/wiper of the cleaning mechanism 504 may be positioned within and/or adjacent the portion of the scanning view in which no primary radiation is emitted. In this way, most if not all of an entire inner wall (e.g., 406 in FIG. 4) of the shroud 506, which defines the bore 508, may be cleaned during an examination of the object.

Stated differently, the cleaning mechanism 504 may be configured to synchronously and/or asynchronously rotate with the radiation source 512 and/or the detector array 514 and may be positioned within and/or adjacent a portion of the scanning field in which little to no primary radiation traverses (e.g., 450 in FIG. 4). As the radiation source 512 and/or the detector array 514 rotate, the cleaning mechanism 504, or at least a portion of the cleaning mechanism 504, lead or follow, for example, the source 512 and/or detector array 514 such that the cleaning mechanism 504 remains outside the wedge (e.g., in area(s) 450 in FIG. 4). Thus, a brush and/or wiper, etc., for example, can substantially continuously clean most if not all of the circumference of the bore during an examination while attenuating little to no radiation. It will be appreciated that in such an embodiment (e.g., where at least a portion of the cleaning mechanism is coupled to the rotating gantry), the cleaning mechanism, or a portion thereof, can "scrape clean" or "brush away" debris from the inner sidewall 406 of the shroud 506 when an examination is not occurring (e.g., by merely rotating the gantry).

FIGS. 8-11 illustrate such an environment 800 (e.g., where a cleaning mechanism 802 is operably coupled to the rotating gantry or other device configured to rotate synchronously with the radiation source 804 and/or the detector array 806). The example environment illustrates an interior wall 808 (e.g., 406 in FIG. 4) of a shroud (e.g., 506 in FIG. 5) that may define a bore (e.g., 508 in FIG. 5), also referred to as a window (e.g., a hollow cavity through the shroud in which an object under examination is placed), in the object examination apparatus (e.g., 502 in FIG. 5). The interior wall 808 (and the rest of the shroud) is generally substantially stationary during an examination of an object.

Figures 8, 9:
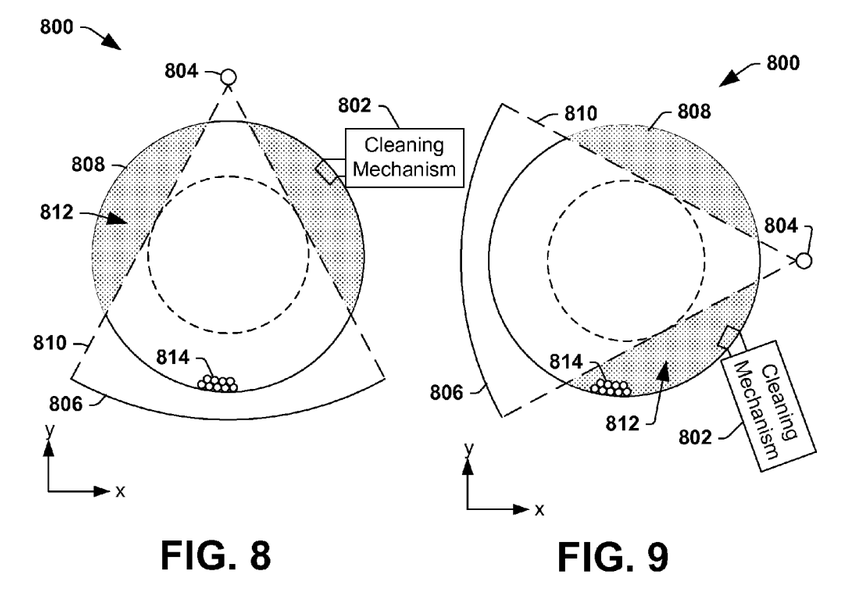
FIG. 8 illustrates a two-dimensional front view of an object examination apparatus having a cleaning mechanism attached thereto for cleaning an inner wall of a shroud of the object examination apparatus.
FIG. 9 illustrates a two-dimensional front view of an object examination apparatus having a cleaning mechanism attached thereto for cleaning an inner wall of a shroud of the object examination apparatus.
Figure 10:
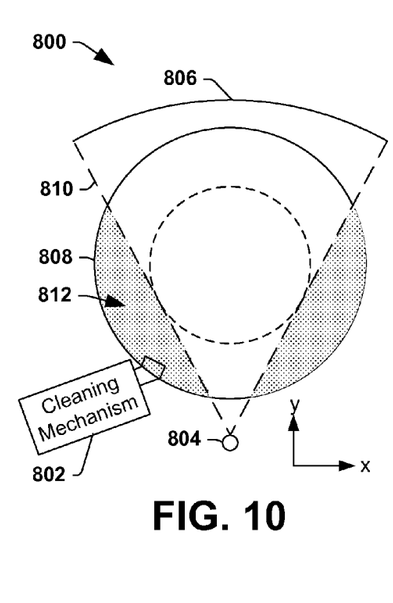
FIG. 10 illustrates a two-dimensional front view of an object examination apparatus having a cleaning mechanism attached thereto for cleaning an inner wall of a shroud of the object examination apparatus.
Figure 11:
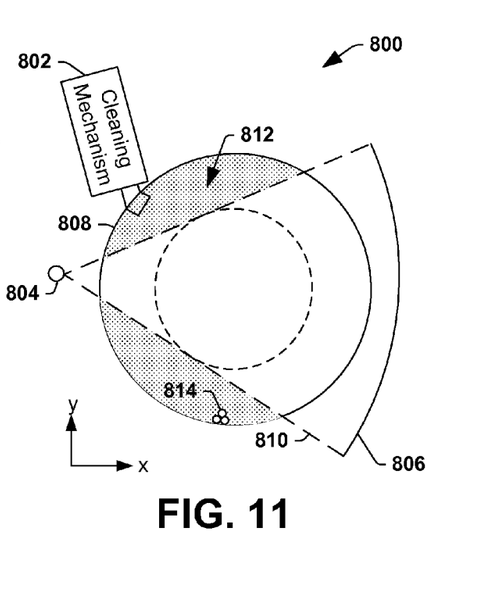
FIG. 11 illustrates a two-dimensional front view of an object examination apparatus having a cleaning mechanism attached thereto for cleaning an inner wall of a shroud of the object examination apparatus.

The radiation source 804 and/or the detector array 806 may be physically coupled to a rotating gantry (not shown) and may be hidden from view by the shroud once the radiographic examination apparatus is manufactured. During an examination of an object, the rotating gantry rotates, causing the radiation source 804 and detector array 806 to rotate synchronously (e.g., such that the orientation of the radiation source 804 and detector array 806 remains substantially constant relative to one another). It will be appreciated that FIGS. 8-11 are intended to represent one full rotation of the radiation source 804 and/or the detector array 806, with respective representations being turned 90 degrees. That is, FIG. 8 illustrates the radiation source 804 and the detector array 806 at first positions. FIG. 9 illustrates the radiation source 804 and the detector array 806 at second positions, the second positions being a 90 degree rotation from the first positions. FIG. 10 illustrates the radiation source 804 and the detector array 806 at third positions, the third positions being a 90 degree rotation from the second positions. FIG. 11 illustrates the radiation source 804 and the detector array 806 at fourth positions, the fourth positions being a 90 degree rotation from the third positions (e.g., and a 270 degree rotation from the first position).

As illustrated, during an examination of an object, radiation 810 is emitted in a fan-shaped or cone-shaped beam, causing primary radiation (e.g., the radiation used to acquire information about the object under examination) to substantially resemble a "wedge" or "fan" and not impinge a portion 812 of a scanning field.

It will be appreciated that by locating or inserting a portion of the cleaning mechanism 802 outside of the wedge or into the shadowed portion 812 of the scanning field (e.g., such that it makes contact with the interior wall 808 of the shroud that defines the bore (e.g., whereon debris 814 and/or fluid may accumulate)) and by rotating the cleaning mechanism 802 synchronously with the rotating gantry, the radiation source 804, and/or the detector array 806, the inserted portion of the cleaning mechanism 802 may remain within the scanning field for an extended period of time during the examination (e.g., during the entire examination) without interfering with (e.g., attenuating) primary radiation that is emitted by the radiation source 804 and detected by the detector array 806.

For example, as illustrated in FIG. 9, as the radiation source 804 and the detector array 806 rotate by ninety degrees relative to their starting position as illustrated in FIG. 8, so too does the cleaning mechanism 802 and the shadowed portions 812 of the scanning field (e.g., wherein there is little to no primary radiation). Moreover, because the shroud itself (e.g., including its interior wall 808) remains substantially stationary during the examination, the debris 814 that has accumulated on the interior wall 808 remains substantially stationary.

As illustrated in FIG. 10, as the radiation source 804 and the detector array 806 rotate by 180 degrees relative to their starting position, so too does the cleaning mechanism 802 and the shadowed portion 812 of the scanning field, causing debris 814, which was resting on the interior wall 808 of the shroud, to be displaced (e.g., pushed off an edge of the shroud and/or suctioned into a portion of the cleaning mechanism 802, etc.). Thus, the cleaning mechanism 802 removes (at least some) debris from the interior wall 808 of the shroud with little to no interference with the scan. FIG. 11 illustrates that, after debris have been cleaned away (in FIG. 10), debris may nevertheless begin to re-accumulate such that the cleaning mechanism or a portion thereof may again remove at least some debris during the next rotation.

It will be appreciated that while FIGS. 8-11 merely illustrate the cleaning mechanism 802 removing debris 814 from a small portion of the interior wall 808 of the shroud, it will be appreciated that the cleaning mechanism 802 may actually remove debris 814 and/or fluids from a much larger portion of the interior wall 808 (e.g., such as the entire interior wall 808), since the cleaning mechanism 802 is rotating in synchronization with the radiation source 804 and the detector array 806. Moreover, while a portion of the cleaning mechanism 802 is merely illustrated in one of the two shadowed portions 808, it will be appreciated that in another embodiment, both shadowed portions 808 may comprise one or more portions of a cleaning mechanism 802.

Further, in an embodiment where the cleaning mechanism 802 is configured to be rotated (e.g., by being coupled to the rotating gantry and/or being coupled to another apparatus configured to rotate synchronously or asynchronously with the rotating gantry), it will be appreciated that the cleaning mechanism 802 may comprise a storage compartment(s) configured to store liquid and/or gas, for example. That is, in one example, the cleaning mechanism 802 may comprise one or more reservoirs for storing liquids and/or gases during the examination. In this way, the cleaning mechanism 802 can be rotated without the concern for liquid or gas pipes that may be necessary to supply fluid or gas to the cleaning mechanism 802 if the cleaning mechanism 802 did not have a reservoir for storing such fluid and/or gas.

Figure 12:
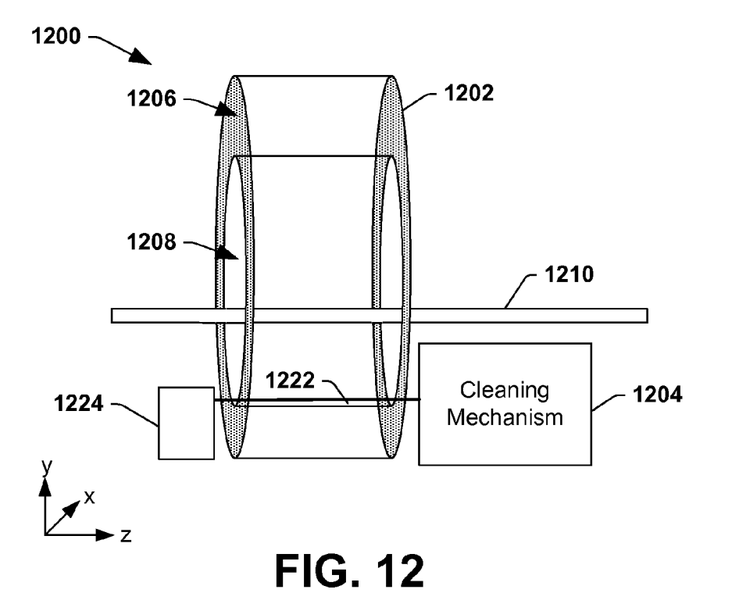
FIG. 12 illustrates a three-dimensional side view of an object examination apparatus and an adjacent cleaning mechanism for dispensing liners into a bore in the object examination apparatus.

FIG. 12 illustrates yet another environment 1200 illustrating an example cleaning mechanism 1204 of a radiographic examination apparatus. As illustrated herein, the cleaning mechanism 1204 comprises a liner dispenser configured to dispense liners 1222, at least a portion of which may be situated in the bore 1208 between the shroud 1206 and the object under examination (e.g., residing on the support article 1210). The liners 1222 are configured to collect debris and may be periodically replaced with a new liner as is warranted (e.g., to mitigate the accumulation of debris and/or fluid).

Because the liners 1222 are generally within a scanning field of the object examination device 1202 and may be exposed to radiation, the liners 1222 are generally comprised of a material that is substantially transparent to the radiation. For example, in one embodiment, the liners 1222 are comprised of cloth because cloth is substantially transparent to radiation and is durable enough to withstand an accumulation of debris (e.g., wood chips, sawdust, trimmings, etc.) while maintaining sufficient structural integrity to remove debris accumulated thereon when the cloth liner is itself removed from the shroud 1206. It will be appreciated, however, that one or more other materials having properties suitable for use as liners (e.g., plastic) are also contemplated.

In the illustrated embodiment, a second device 1224 is positioned opposite the cleaning mechanism 1204 and is configured to receive used liners. For example, in one embodiment, the second device is configured to automatically pull a section of a liner 1222 that has accumulated a predetermined amount of material (e.g., as measured by the cleaning mechanism, the workstation, and/or another device, for example) and/or that has been in the scanning field for a predetermined period of time and to replace it with a new section of liner that has not yet accumulated debris. It will be appreciated that such automation may allow the liner 1222 to be replaced during an examination of an object (e.g., during a time when radiation is being emitted).

In another embodiment, the portion of the liner 1222 that is within the scanning field may simply be replaced with a clean portion of the liner 1222 manually (e.g., by a user of the device). Thus, the second device 1224 may be unnecessary.

It will be appreciated to those skilled in the art that while a cleaning mechanism is described herein for cleaning a shroud, in some embodiments, the shroud itself may be designed to mitigate the amount of debris, fluid, etc. that accumulates within the scanning field and/or the design of the shroud may assist the cleaning mechanism in the collection of debris, fluid, etc. Thus, the shroud itself may be considered the cleaning mechanism, or at least be considered a portion of the cleaning mechanism (e.g., where other cleaning mechanisms, such as a liquid dispenser, are used in conjunction with a tapered shroud).

Figure 13:
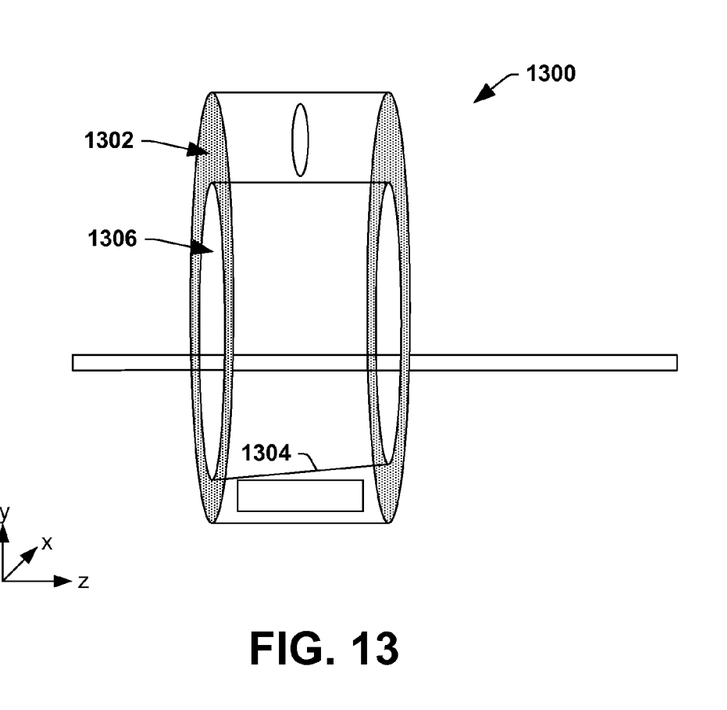
FIG. 13 illustrates a three-dimensional side view of an object examination apparatus having a shroud comprising at least one tapered edge.

FIG. 13 illustrates an object examination apparatus 1300 (e.g., 102 in FIG. 1) having a tapered shroud 1302. That is, as illustrated herein, at least a portion of an interior wall 1304 of the shroud 1302 (e.g., an edge of the shroud that defines a bore 1306 through which an object under examination is passed) may be tapered. The degree of the taper (e.g., the degree of the slant or slope), the direction of the taper, and/or the length of the taper may depend upon numerous factors including, but not limited to, the type of debris and/or fluid that that may collect on the shroud, the type of cleaning mechanism, and/or the orientation of the cleaning mechanism relative to the object examination apparatus 1300, for example. For example, where the cleaning mechanism is configured to dispense gas and/or liquid toward the shroud, the shroud may be tapered away from the cleaning mechanism from edge-to-edge such that gravity (e.g., with the aid of the dispensed matter) causes the debris and/or fluid to roll off the opposite side of the object examination apparatus 1300 relative to the cleaning mechanism. In another embodiment, where the cleaning mechanism comprises a suction mechanism, for example, the shroud may be tapered toward the cleaning mechanism such that gravity (e.g., along with the suctioning) causes the debris/fluid to roll towards the cleaning mechanism and be vacuumed by the cleaning mechanism, for example.

Figure 14:
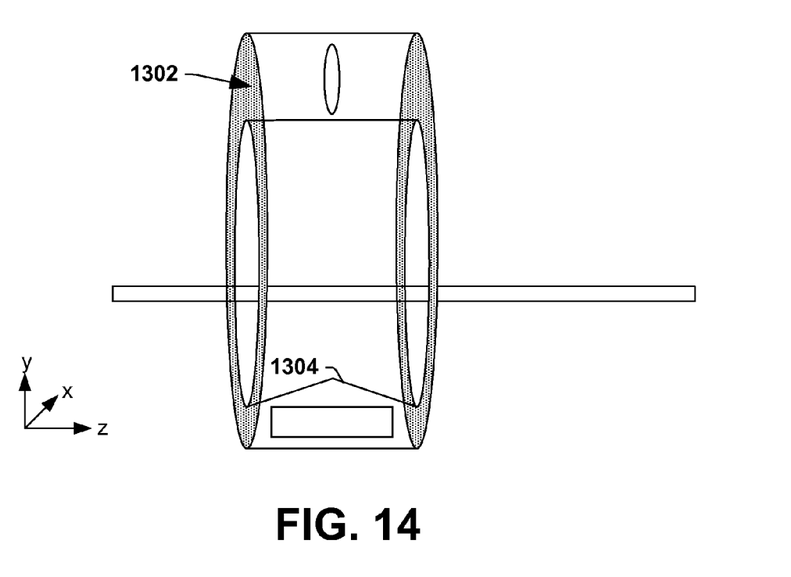
FIG. 14 illustrates a three-dimensional side view of an object examination apparatus having a shroud comprising at least one tapered edge.

It will be appreciated that because the shroud is substantially stationary throughout the examination of the object, merely a bottom portion of a shroud can be tapered as illustrated herein. However, in one embodiment, the entire inner surface (e.g., including upper walls) of the shroud may be tapered (e.g., to make the manufacturing of the shroud easier and/or more uniform. Moreover, it will be appreciated that while the example shroud 1302 illustrates substantially the entire z-dimension of the interior wall 1304 along a bottom portion of the shroud 1302 being tapered, it will be appreciated that in another embodiment, less than the entire z-dimension can be tapered. For example, in another embodiment, merely 50% of the z-dimension is tapered. Moreover, as illustrated in FIG. 14, the type of tapering may differ depending upon the application and/or whether other cleaning mechanisms are used in conjunction with the tapered shroud. For example, as illustrated in FIG. 14, the interior wall 1304 of a bottom edge of the shroud may be tapered to be an inverted v-like formation.

Further, other features can be applied to the shroud 1302 to improve the cleanliness of the shroud 1302. For example, the shroud 1302 may be comprised of an antistatic material, such as an antistatic plastic to mitigate electrostatic buildup of debris on the shroud. It will be appreciated to those skilled in the art that electrostatic buildup may occur along any and/or all edges of the shroud 1302 and may cause debris to accumulate in portions of the shroud 1302 where it would not accumulate but for the electrostatic buildup (e.g., because of gravity). For example, gravity would generally cause the debris to collect on a surface of the shroud 1302 adjacent a bottom portion of the bore (e.g., a portion of the bore nearest the ground). However, electrostatic buildup may cause debris to accumulate on walls adjacent a side portion of the bore or a top portion of the bore. Thus, debris that would normally fall to the bottom instead clings to other portions of the shroud 1302 due to electrostatic buildup. By manufacturing a shroud 1302 comprised of an antistatic material, electrostatic buildup may be mitigated (e.g., causing the debris to be deposited merely on a surface adjacent a bottom of the bore where it may more easily be collected, for example). Moreover, in another embodiment, an electric source may be configured to energize portions of the shroud 1302 where electrostatic buildup generally occurs. In this way, the shroud 1302 becomes conductive, inhibiting the electrostatic buildup of debris on the conductive portions of the shroud 1302. Thus, to mitigate electrostatic buildup, the shroud 1302 itself may be comprised of an antistatic material and/or an electrical current can be supplied to the shroud 1302 to energize the shroud 1302, causing it to become conductive, for example. Similarly, the shroud may be grounded so that electrostatic charge does not accumulate thereon. In this manner, it would be more likely for debris to accumulate (via gravity) on a bottom surface of the shroud (e.g., so that it can be abated via one or more cleaning mechanisms as described herein) rather than other locations of the shroud.

Figure 15:
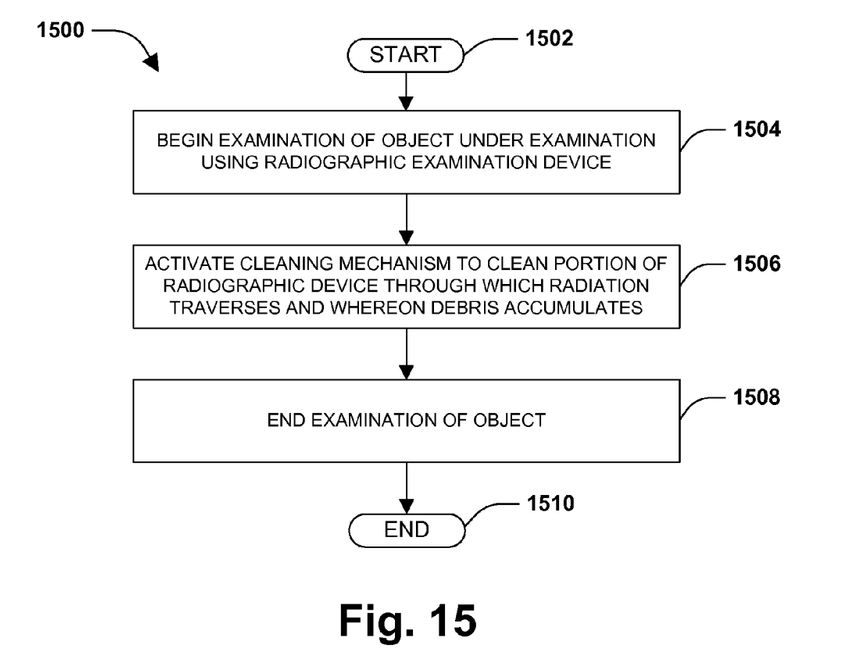
FIG. 15 is a flow diagram illustrating an example method for cleaning a radiographic examination device.

FIG. 15 illustrates an example method 1500 for cleaning a radiographic examination device, such as the radiographic examination device illustrated in the example environment 100 in FIG. 1. The example method begins at 1502, and an examination of an object under examination using the radiographic examination device begins at 1504. During the examination of the object, radiation is emitted from one or more radiation sources into an examination region wherein the object under examination resides. Radiation that traverses the object is subsequently detected by a detector array positioned on the opposite side of the examination device relative to the radiation source(s). Thus, an examination may be said to comprise the emission and detection of radiation.

In one embodiment, during the examination of the object, the radiation source and/or the detector array are rotated (e.g., via a rotary gantry to which the radiation source and detector array are physically coupled) about an axis (e.g., parallel to an axis through which the object is conveyed). For example, referring to FIG. 1, the radiation source and detector array may be rotated in an x, y plane about an axis extending in the z-dimension. It will be appreciated that by rotating the radiation source and/or detector array in such a fashion, the object may be examined from a plurality of angles and volumetric data representative of the object may be yielded. Stated differently, by examining the object from a plurality of angles, a three-dimensional image, for example, of the object may be acquired such that a volumetric coordinate of targets of interest within the object under examination can be identified.

The example method 1500 further comprises activating a cleaning mechanism configured to clean a portion of the radiographic examination device through which radiation traverses and whereon debris accumulates. For example, referring to FIG. 4, a cleaning mechanism may be configured to clean an inner wall of a shroud that surrounds the rotating gantry, where the inner wall defines a bore through which the object under examination passes.

Generally, activating the cleaning mechanism comprises activating an actuator, such as a pneumatic actuator and/or an electric actuator, for example. The cleaning mechanism (or more specifically the actuator) may be activated via a signal sent from another portion of the radiographic examination device, such as from a workstation (e.g., 134 in FIG. 1) and/or an object examination apparatus (e.g., 102 in FIG. 1), or it may be self-activating, where the cleaning mechanism activates without the aid of information from an external device. For example, in one embodiment, the cleaning mechanism may comprise a laser or other monitoring device configured to monitor an amount of debris, fluid, etc. on the portion of the radiographic device to be cleaned. When the laser or other monitoring device senses a predetermined amount of buildup, the cleaning mechanism may be activated to clean the portion of the radiographic device whereon the debris has accumulated. In another embodiment, the amount of debris that builds up on the shroud is monitored by a workstation, for example, that activates or triggers the cleaning mechanism to begin cleaning the shroud. For example, the workstation may monitor the amount of radiation that is being detected, and if the amount of radiation that is detected by a specified portion(s) of the detector array (e.g., such as one or more edges of the detector array that do not generally detect radiation traversing the object) dips below a predetermined threshold and/or changes by a predetermined threshold, for example, the workstation may activate the cleaning mechanism (e.g., because a build-up of debris has caused the drop in the amount of radiation detected). It will be appreciated that where the cleaning mechanism is activated during an examination and attenuates radiation that otherwise would not be attenuated, interpolation and/or other correction techniques can be implemented to account for the intervening of the cleaning mechanism (or portion thereof) during the examination as described herein.

At 1506 in the example method 1500, a portion of the radiographic examination device through which radiation traverses is cleaned during the examination. That is, while radiation is being emitted into a scanning field of the radiographic examination device, a portion of the shroud within and/or adjacent the scanning field is cleaning. For example, as illustrated in FIGS. 5-11, a bottom, interior wall of a shroud (e.g., that defines a bore in the shroud) may be cleaned to remove fluids and/or debris that have accumulated on the shroud during an examination of the object and/or other objects.

As described above, there are numerous techniques contemplated for cleaning the shroud, or more generally, the portion of the radiographic examination device that is to be cleaned. For example, in one embodiment, a gas and/or a liquid is dispersed towards the portion of the radiographic examination device that is to be cleaned. Such gas and/or liquid is designed to displace the particulates and/or fluid(s) that have accumulated on the radiographic examination device. In another embodiment, the debris and/or fluid(s) are suctioned away from the portion of the shroud that is to be cleaned (e.g., the cleaning mechanism acts similarly to a vacuum). In yet another embodiment, the debris and/or fluid(s) are wiped and/or brushed away from the portion of the radiographic examination device that is to be cleaned.

It will be appreciated that because the object is being examined during the cleaning (e.g., because radiation is being emitted into the scanning field while the portion of the radiographic examination apparatus is being cleaned), special considerations may be taken to mitigate the probability that the cleaning process interferes with (e.g., attenuates) the radiation. For example, in one embodiment, the cleaning mechanism is merely activated and/or the portion of the radiographic examination device is merely cleaned when radiation is not traversing said portion of the device. That is, referring to FIG. 4, merely portions of the radiographic examination device comprised within/adjacent to the shaded portions of the scanning field (e.g., outside of the wedge) may be cleaned. Thus, when the portion to be cleaned is being exposed to radiation (e.g., at least primary radiation), the cleaning mechanism may be deactivated or turned off (e.g., and debris may continue to accumulate). However, when the portion to be cleaned is not being exposed to radiation (e.g., because the radiation source is emitting radiation away from the portion to be cleaned), the cleaning mechanism may be activated and/or the cleaning mechanism may proceed to clean the unexposed portion of the radiographic examination apparatus (e.g., while the radiation is still be emitted in another portion of the scanning field).

Moreover, as described above with respect to FIGS. 8-11, in one embodiment at least a portion of the cleaning mechanism (such as the nozzle and/or the brush) may be rotated about the object under examination during the examination of the object (e.g., following a path coincident with the path traveled by the radiation source and/or the detector array). For example, in one embodiment, the cleaning mechanism, or a portion thereof, may be attached to the rotating gantry such that the cleaning mechanism, or a portion thereof, protrudes through the shroud to clean an interior sidewall of the shroud as the gantry rotates. In this embodiment, said protruding cleaning portion of the cleaning mechanism is offset from the source and detector on the rotating gantry so that little to no emitted radiation impinges thereon. In this manner, an inner surface can be cleaned when the gantry is rotated with little to no interference to an examination. In this embodiment the interior sidewall of the shroud may also be cleaned (e.g., by rotating the gantry) when an examination is not being performed.

It will be appreciated that other special considerations may also be taken if a portion of the cleaning mechanism, such as a removable liner, is positioned within the scanning field. For example, in one embodiment, the portion of the cleaning mechanism that is positioned within the scanning field is comprised of a material having properties that make it substantially transparent to radiation (such as a low density plastic). In this way, radiation may traverse that portion of the cleaning mechanism positioned within the scanning field without being substantially attenuated by the cleaning mechanism.

Moreover, in one embodiment, where a portion of the cleaning mechanism interferes with radiation, data yielded from the detected radiation may be altered and/or updated to correct for the interference. For example, in one embodiment, the position of the portion of the cleaning mechanism that interfered with the radiation may be determined, or calculated, and based upon the amount of radiation in areas surrounding the determined position of the cleaning mechanism, interpolation may be performed to estimate the amount of radiation that should have been detected in the area wherein the cleaning mechanism was located. Thus, where a portion of the cleaning mechanism interferes with radiation (e.g., causing less radiation to be detected than would have been detected without the interference), interpolation and/or other correction techniques may be performed using suitable analytic, iterative, or other appropriate approximation techniques known to those skilled in the art to correct the data yielded for a portion of the detector that detected less radiation as a result of the interference.

In yet another embodiment, cleaning the portion of the radiographic examination device comprises replacing a liner situated between an object under examination and the detector array and/or radiation source. The liner, which may be made of cloth or another material that is substantially transparent to radiation, collects debris and/or fluid and may be replaced when a sufficient amount of debris has collected on the liner and/or a predetermined amount of time has elapsed since the liner was last replaced. It will be appreciated that because at least a portion of the liner is positioned in a scanning field of the radiographic examination device, a user may not be able to replace the liner. Thus, in one embodiment, the liner is replaced using one or more mechanical devices. For example, in one embodiment, rolling pins may be placed on two sides of the radiographic examination apparatus (e.g., with the bore positioned between the two sides). Wrapped around the first rolling pin is a clean portion of the liner, and the first rolling pin is configured to dispense the liner into the bore in the radiographic examination device. The second rolling pin is configured to pull the liner through the bore (e.g., causing the clean portion of the liner to be unwound from the first rolling pin), such that a dirty portion of the liner is replaced with a clean portion of the liner, for example. The second rolling pin may also be configured to receive the dirty portion of the liner (e.g., such that the dirty portion of the liner is wrapped around the second rolling pin or otherwise be removed from the bore).

At 1508 in the example method 1500 the examination of the object ends (e.g., radiation stops being emitted and/or detected), and at 1510 the example method 1500 ends.

It will be appreciated that while the aforementioned method provides for cleaning a portion of the radiographic examination device during an examination of the object (e.g., while radiation is being emitted and/or detected), the instant application, including the claimed methods, are not intended to be so limited. That is, to the extent possible, the techniques described herein may be performed before and/or after the examination as well. Thus, the portion of the radiographic examination device that is to be cleaned may be cleaned before, during, and/or after the examination of the object.

Moreover, the words "example" and/or "exemplary" are used herein to mean serving as an example, instance, or illustration. Any aspect, design, etc. described herein as "example" and/or "exemplary" is not necessarily to be construed as advantageous over or better than other aspects, designs, etc. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, it will be appreciated that at least one of A and B and/or the like generally means A or B or both A and B.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An apparatus for cleaning a radiation system, comprising:
    a mechanized cleaning mechanism coupled to the radiation system and configured to clean at least a portion of a shroud of the radiation system, the portion of the shroud situated at least one of:
        between an object under examination and a detector array of the radiation system, or
        between the object and a radiation source of the radiation system.

2. The apparatus of claim 1, wherein the mechanized cleaning mechanism comprises a wiper configured to clean the portion of the shroud by contacting a surface of the shroud.

3. The apparatus of claim 2, wherein the wiper is positioned outside of a scanning field of the radiation system during a time when the wiper is not cleaning the portion of the shroud and inside of the scanning field during a time when the wiper is cleaning the portion of the shroud.

4. The apparatus of claim 2, wherein at least a portion of the wiper is positioned in a scanning field of the radiation system, the portion of the wiper configured to rotate relative to the object.

5. The apparatus of claim 4, wherein the portion of the wiper is configured to rotate synchronously with a rotating gantry portion of the radiation system.

6. The apparatus of claim 1, wherein the mechanized cleaning mechanism comprises a gas dispenser configured to clean the portion of the shroud by dispensing a gas.

7. The apparatus of claim 1, wherein the mechanized cleaning mechanism comprises a liquid dispenser configured to clean the portion of the shroud by dispensing a liquid.

8. The apparatus of claim 1, wherein the mechanized cleaning mechanism comprises at least one of a gas dispenser comprised within a rotating gantry portion of the radiation system or a liquid dispenser comprised within the rotating gantry portion of the radiation system.

9. The apparatus of claim 1, wherein the mechanized cleaning mechanism comprises an electrical source configured to energize the shroud.

10. The apparatus of claim 1, wherein the mechanized cleaning mechanism is tapered in a direction substantially parallel to a direction in which the object is conveyed through the radiation system.

11. The apparatus of claim 1, wherein the mechanized cleaning mechanism comprises one or more removable liners for positioning between the shroud and the object.

12. A method for cleaning a radiation system, comprising:
beginning an examination of an object under examination using the radiation system;
cleaning a portion of the radiation system through which radiation traverses during the examination by rotating a cleaning mechanism synchronously with a rotation of at least one of a detector array or a radiation source of the radiation system; and
ending the examination.

13. The method of claim 12, wherein the cleaning mechanism is rotated within a scanning field of the radiation system.

14. The method of claim 12, comprising:
maintaining the cleaning mechanism in a scanning field of the radiation system during at least some of the examination.

15. The method of claim 12, wherein the cleaning comprises:
applying an electrical current to at least a portion of a shroud that surrounds an examination region of the radiation system.

16. A method for cleaning a radiation system, comprising:
identifying debris on a portion of the radiation system based on a change in an amount of radiation detected by a detector array of the radiation system;
activating a mechanized cleaning mechanism coupled to the radiation system to clean the portion of the radiation system responsive to the identifying debris; and
cleaning the portion of the radiation system based upon the activating.

17. The method of claim 16, wherein the cleaning comprises:
cleaning the portion of the radiation system during an examination of an object by the radiation system.

18. The method of claim 16, wherein the activating comprises:
activating at least one of a gas dispenser or a liquid dispenser.

19. The method of claim 16, wherein the activating comprises:
activating a rotating gantry portion of the radiation system causing the rotating gantry portion and at least a portion of the mechanized cleaning mechanism coupled to the rotating gantry portion to rotate synchronously about an object under examination.

20. The apparatus of claim 1, comprising:
a sensor coupled to the radiation system and configured to detect debris on the portion of the shroud and the mechanized cleaning mechanism configured to clean the portion of the shroud when the sensor detects debris on the portion of the shroud.

21. The apparatus of claim 20, wherein the sensor comprises a laser.

22. The apparatus of claim 1, wherein the mechanized cleaning mechanism is configured to clean the portion of the shroud based upon an amount of radiation detected by a detector array of the radiation system.

* * * * *